US006598799B1

(12) United States Patent
Jang

(10) Patent No.: US 6,598,799 B1
(45) Date of Patent: Jul. 29, 2003

(54) SYSTEM FOR TRACKING PATIENT CONFIDENTIALITY FORMS

(76) Inventor: Jin S. Jang, 1201 Pebble Beach Dr., Elkton, MD (US) 21921

( * ) Notice: Subject to any disclaimer, the term of this patent is extended or adjusted under 35 U.S.C. 154(b) by 154 days.

(21) Appl. No.: 09/945,687

(22) Filed: Sep. 5, 2001

Related U.S. Application Data
(60) Provisional application No. 60/230,714, filed on Sep. 7, 2000.

(51) Int. Cl.[7] .................................................. G07G 1/00
(52) U.S. Cl. .................................................. 235/462.25
(58) Field of Search ............................... 235/383, 380, 235/462.45, 375, 472.01; 705/2, 8, 39; 707/104.1; 715/508, 531

(56) References Cited

U.S. PATENT DOCUMENTS

| | | | |
|---|---|---|---|
| 4,158,194 A | | 6/1979 | McWaters et al. |
| 4,180,204 A | | 12/1979 | Koenig et al. |
| 4,339,745 A | | 7/1982 | Barber et al. |
| 4,621,189 A | | 11/1986 | Kumar et al. |
| 4,858,121 A | * | 8/1989 | Barber et al. .................. 705/2 |
| 4,893,270 A | * | 1/1990 | Beck et al. .................... 700/90 |
| 5,297,202 A | | 3/1994 | Kapp et al. |
| 5,319,543 A | * | 6/1994 | Wilhelm ........................ 705/3 |
| 5,327,341 A | * | 7/1994 | Whalen et al. ................. 705/3 |
| 5,361,202 A | * | 11/1994 | Doue ............................ 705/3 |
| 5,408,078 A | | 4/1995 | Campo et al. |
| 5,430,276 A | | 7/1995 | Ohtani et al. |
| 5,448,044 A | | 9/1995 | Price et al. |
| 5,625,555 A | | 4/1997 | Davis |
| 5,772,585 A | * | 6/1998 | Lavin et al. ................. 600/300 |
| 5,895,452 A | | 4/1999 | Lum |
| 5,950,168 A | * | 9/1999 | Simborg et al. ................ 705/3 |
| 6,050,490 A | | 4/2000 | Leichner et al. |
| 6,073,106 A | * | 6/2000 | Rozen et al. ................... 705/3 |
| 6,405,165 B1 | * | 6/2002 | Blum et al. .................. 704/235 |
| 6,434,569 B1 | * | 8/2002 | Toshimitsu et al. ......... 707/100 |
| 6,464,136 B2 | * | 10/2002 | Walsh ........................ 235/380 |
| 2002/0027162 A1 | * | 3/2002 | Jang ........................... 235/383 |

FOREIGN PATENT DOCUMENTS

| | | |
|---|---|---|
| DE | 32 14621 A1 | 10/1983 |
| GB | 1 603 767 | 11/1981 |
| JP | 4-58398 | 2/1992 |
| JP | 5-46871 | 2/1993 |

* cited by examiner

Primary Examiner—Thien M. Le
(74) Attorney, Agent, or Firm—Richard C. Litman

(57) ABSTRACT

A validating tracking system for tracking deliveries of prescription medications from a pharmacy includes a cash register, sniffer, scanner, credit card machine, monitor, computer, and printer. The scanner scans prescription numbers from a prescription bag at the time of delivery. The sniffer intercepts a copy of the scanned prescription numbers as transmitted from the scanner to the cash register, and displays the prescription numbers and identification of medications in a patient consultation form displayed on the monitor. The monitor is capable of digitizing and electronically storing a customer signature traced-on the form on the screen with a stylus. The computer maintains a database including a list of all prescription numbers ordered by the patient and a copy of the consultation form with the digitized signature showing date and time of delivery.

12 Claims, 1 Drawing Sheet

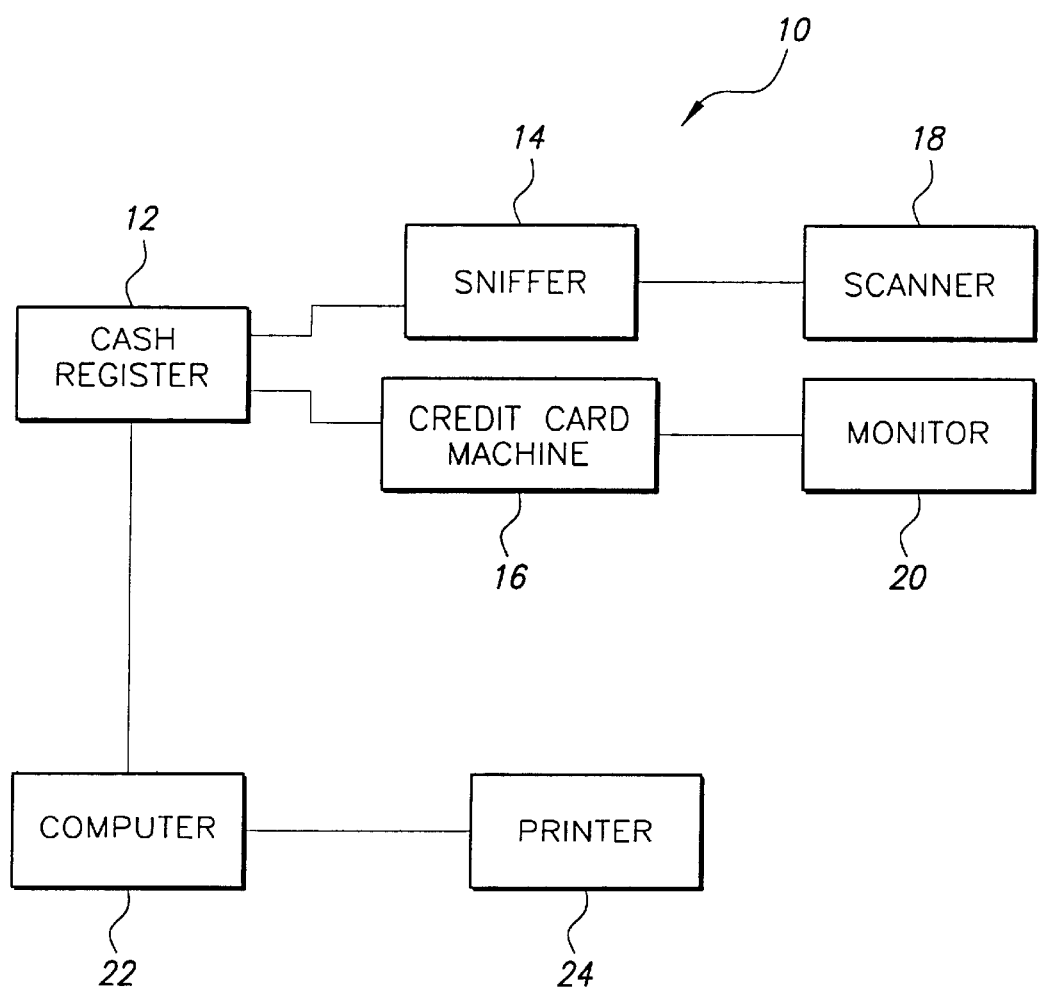

SYSTEM FOR TRACKING PATIENT CONFIDENTIALITY FORMS

CROSS-REFERENCE TO RELATED APPLICATION

This application claims the benefit of U.S. Provisional Patent Application Serial No. 60/230,714, filed Sep. 7, 2000.

BACKGROUND OF THE INVENTION

1. Field of the Invention

The present invention relates generally to a prescription transaction data system, and more specifically to a system for recording and tracking prescription transactions.

2. Description of Related Art

The invention relates to a system and a method for processing signature-based transactions. More particularly, a merchant's records of delivery of goods, such as the delivery of prescription drugs, can be generated and maintained electronically without generation or use of paper records except those delivered to customers at the point of sale.

In retailing and similar areas, the volume of transactions is often such that management of paper records is burdensome. Therefore paper records are being replaced by digital storage media whenever feasible. However, digital storage media have not been able to eliminate the need for paper storage in many financial transactions requiring consumer approval. Typical examples are transactions involving account debit, i.e., including checks and charge receipts. In such transactions, paper documentation bearing a signature has continued to be the norm. The storage and retrieval of such records is both inefficient and costly.

While techniques have been developed for producing digitized facsimiles of human signatures and processing thereof, there has been no practical means of correlating a digitized signature with a specific transaction. Only by a copy of the approving signature thereon has it been possible to satisfy the commercial need for proof of an obligation. Thus, paper records have persisted in the face of strong incentives for their elimination.

In the area of retail marketing of prescription drugs, there is a particular need for an automated system for tracking the order and delivery of drugs. Many consumers require several different prescription medications, have multiple prescriptions for the same medication, or require refills on a prescription. In many retail establishments there is no automated system for recording the date and time of delivery of the prescription medication to the consumer and the name of the person who accepted delivery. Consequently, when a consumer asks the clerk whether an order is ready, a manual search must be made of prescription medications waiting for customer pickup or waiting for preparation by the pharmacist. If there is a dispute between the consumer and the pharmacy about whether the medication has been picked up already, the pharmacy often has no record of the exact date and time the medication was picked up and the identity of the receiver of the prescription. Alternatively, if the pharmacy does have such records, they are paper records and require an undue amount of time to locate. Consequently, there is a need for an automated system for recording and tracking the delivery of goods to the consumer, and particularly for maintaining confidential records and forms, such as a patient's prescriptions.

The relevant art of interest will be described in the order of perceived relevance to the present invention.

Japanese Patent Application No. 5-46871 published on Feb. 26, 1993, for Tatsuo Morimoto describes a system eliminating a separate printer by miniaturizing a point-of-sale terminal or cash register to incorporate a central processing unit (CPU) with an operator's display, an elevated and larger customer's display on top, a journal printer inside, a keyboard, a memory, an IC card reader and writer, and a bar code reader. Sales information inputted from the keyboard or the bar code reader is transmitted to the IC card reader and writer via the CPU and recording sales information on the IC card. The system is distinguishable for recording sales information and eliminating an external printer device.

U.S. Pat. No. 5,448,044 issued on Sep. 5, 1995, to James F. Price et al. describes a signature capture pad for gathering signature data associated with customer transactions including a digitizer, microprocessor, and a plurality of serial ports, and may be connected to a point of sale terminal, such as an electronic cash register. The device is distinguishable for its limited use to a signature capture pad.

U.S. Pat. No. 6,050,490 issued on Apr. 18, 2000, describes a handheld writing device and related data entry system. A digital electronic clipboard is used to mount pages or forms utilized in forms processing applications, such as inventory tracking. A stylus having a writing tip and a bar code scanning mechanism at its opposite tip is used to enter data on the pages and scan the bar codes. The system is distinguishable for its required stylus having a specific capacity.

U.S. Pat. No. 4,158,194 issued on Jun. 12, 1979, to Lynn McWaters et al. describes an optical recognition system, wherein total data entry is accomplished through a hand held unit. The unit includes an optical scanner, a keyboard and a display which communicates with a portable character recognition unit. The system is distinguishable for requiring a portable character recognition unit.

U.S. Pat. No. 4,180,204 issued on Dec. 25, 1979, to Richard W. Koenig et al. describes an automatic inventorying system for automatically inventorying items having coded tags or labels using a character recognition device, such as a wand scanner, in combination with a system for specially marking labels when they have been successfully read and recorded by the scanner. The system comprises a photosensitive dye-forming material on the label and an ultraviolet light-producing flash device on the scanner. The system is distinguishable for being limited to a scanner for marking labels.

U.S. Pat. No. 4,621,189 issued on Nov. 4, 1986, to Rajendra Kumar et al. describes a hand held data entry scanner apparatus having an optical scanning head rotatable on a hand-held keyboard and a liquid crystal display. The apparatus is distinguishable for being limited to a hand-held scanner.

U.S. Pat. No. 5,297,202 issued on Mar. 22, 1994, to Michael A. Kapp et al. describes a method and system for generating a completed payment document ready for signature in image form. The document is signed by a customer, and a copy of the signature is captured in digital form. Thereafter, the signature is encrypted and saved along with a digital record of the transaction. The system is distinguishable for requiring a write input apparatus.

U.S. Pat. No. 5,408,078 issued on Apr. 18, 1995, to James A. Campo et al. describes a portable point of sale terminal that provides all of the usual point of sale terminal functions, but that is entirely field portable. Data pertinent to each purchase can be input to the terminal via a keyboard assembly, a touch-screen display or a signature-capture screen assembly, or via an antenna and radio link from an associated bar code scanner. Data can be communicated to a remote host computer via a separate antenna and radio link. The terminal functions as a portable repeater or a node in a data communications network. The system is distinguishable for its reliance on portability in the field.

U.S. Pat. No. 5,430,276 issued on Jul. 4, 1995, to Kazuo Ohtani-et al. describes an image recording apparatus for (1) reading information for identifying an original document; (2) a recording unit for recording the image of the original document on a recording medium; (3) a selector for selecting a first mode or a second mode; and (4) a controller for causing the recording unit (a) to record the image only when the identifying information is read by the reading means if the first mode is selected, or (b) causing the recording unit to record the image regardless of the reading of the identifying information if the second mode is selected. The apparatus is distinguishable for being limited to image recording.

U.S. Pat. No. 5,625,555 issued on Apr. 29, 1997, to Patrick H. Davis describes a transport vehicle having as an on-board peripheral system coupled to a Local Area Network (LAN), and a data communication system with an adapter for removable coupling of portable data terminals. A LAN data bus provides selective access to the peripherals such as a large area display, a keyboard, a printer, and a data terminal. The data terminals can be removed from the vehicle and still be used. The system is distinguishable for its reliance on LAN.

U.S. Pat. No. 5,895,452 issued on Apr. 20, 1999, to Jackson Lum describes a point of sale system that is freely configurable with a plurality of peripheral input devices. The system includes a computer with an input port coupled to a screen and to an electronic interface connectable to a plurality of peripheral input devices such as a charge coupled device (CCD) barcode reader, a point-of-sale keyboard through an intelligent wedge cable interface, a magnetic stripe reader, an electronic scale, and another input computer keyboard. The system is distinguishable for its freely configurable plurality of peripheral devices.

U.S. Pat. No. 6,058,304 issued on May 2, 2000, to Francis J. Callaghan et al. describes a data entry system that includes a hand held data entry unit having a reading sensor for sensing commands and/or data, rewritable storage for storing information relating to selectable items, a controller (a microprocessor or other processing circuitry), and a display screen for displaying a user readable representation of the commands and/or stored information for a selected item, and a telecommunication interface for telephonic transmission of information relating to a selected item or items from the storage to a remote processing center and for the telephonic information relating to selectable items from the remote processing center to the storage. A telecommunications interface is provided in the hand held unit for cellular or other wireless telephony systems. The system is distinguishable for requiring a telecommunications interface.

U. K. Patent Application No. 1,603,767 published on Nov. 25, 1981, for Francis J. Leaf describes a medical data processing system comprising a first digital data recording and processing computer at a central location, entering medical information, i.e., drug name, by hand on a card having a series of letters and numbers in zones, which are read by machine, and the data fed to the second digital data and recording computer. The system is distinguishable for requiring hand marking input in systemized cards.

German Patent Application No. 3,214,621 A1 published on Oct. 20, 1983, for Siemans AG describes a hand-held combined optical scanner for reading identification labels with both optical character recognition characters and bar codes. The sensor units are contained in separate compartments. The characters are scanned by a matrix of photodiodes and the signals are transmitted to a microprocessor located in the handle. The bar code signals are amplified and converted to digital form initially. The scanner device is distinguishable for being limited to the scanner device.

Japanese Patent Application No. 4-58398 published on Feb. 25, 1992, for Katsuyuki Ono describes a customer management system, wherein a bar code specifies a customer and performs the data transfer between the bar code reader and a customer management device to give an oil supply permission by a radio system. The system is distinguishable for being tailored for furnishing an oil supply to a customer.

U.S. Pat. No. 4,339,745 issued on Jul. 13, 1982, to William D. Barber et al. describes a method and system for producing image data by vibrapreening or laser marking for the automatic recognition of characters on metallic and other specular surfaces having varying roughness and reflectivity. The optical scanner applies normal illumination, and a linear photodiode array detects light reflected normal to the surface and within a narrow acceptance angle, so that characters appear dark and the background light. The detector signal is reprocessed to remove nonuniform background variations and yield data which can be fed to conventional character recognition equipment. The system is distinguishable for the limited use of the optical scanner on metallic and other specular surfaces having roughness.

It is therefore seen that there is a need for a practical method and system for automated recording and tracking of customer orders and delivery of goods.

None of the above inventions and patents, taken either singly or in combination, is seen to describe the instant invention as claimed.

SUMMARY OF THE INVENTION

The present invention is a validating tracking system for tracking the delivery of prescription medication from a pharmacy. The validating tracking system includes a cash register, a sniffer, a scanner, a monitor, and a computer. The cash register is used for calculating a sales price based on a quantity of goods or services purchased. The scanner is attached to the cash register, and is used to scan prescription numbers from a prescription bag at the time of delivery. The sniffer is connected to the system to intercept a copy of the scanned prescription numbers as they are transmitted from the scanner to the register, and displays the prescription numbers only of medications in a patient consultation form displayed on an approximately 4 inch by 8 inch monitor. The patient consultation form also has a space for a customer signature recorded when the consumer receives delivery of the prescription medication. The monitor is capable of receiving digital signals and electronically storing a customer's signature traced on the screen with an appropriate stylus. The computer maintains a database where patient records are stored, including a list of all prescription numbers ordered by the patient. If delivery of a particular prescription is questioned, a copy of the consultation form with the digitized signature showing date and time of delivery can be retrieved.

Accordingly, it is a principal object of the invention to provide a point-of-sale computerized tracking system for tracking purchase transactions of prescription medications.

It is another object of the invention to provide a point-of-sale computerized tracking system for monitoring delivery of prescription medications from a pharmacy.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWING

The sole FIGURE is a block diagram of a point-of-sale integrated tracking system according to the present invention.

Similar reference characters denote corresponding features consistently throughout the attached drawings.

DETAILED DESCRIPTION OF THE PREFERRED EMBODIMENTS

The present invention is an automated tracking system for tracking prescription sales activity at the point of sale. An integrated tracking system 10 according to a preferred embodiment of the present invention is shown in the FIGURE. The tracking system 10 may include a cash register 12, a sniffer 14, credit card machine 16, a scanner 18, a monitor 20, a computer 22, and a printer 24.

Cash Register. The cash register 12 is a conventional electronic cash register. The cash register 12 is preferably connected to a central computer having a database including inventory and price information for prescription drugs, as well as other goods offered for sale by the pharmacy. The cash register 12 serves to calculate a sales price based on the quantity of goods or services purchased.

The Scanner. The scanner 18 is a conventional scanner configured for reading bar codes placed on bags for prescription medication. When a prescription is filled, a bar code label identifying the prescription number is placed on-a prescription bag, and the filled prescription or prescriptions are packaged in the bag. Information concerning the prescription number, including the medication and the name of the patient, and other identifying information, can be entered into a database stored on the computer 22 by the pharmacist when processing the prescription. The scanner 18 is communicatively connected to the cash register 12 for enabling the scanner 18 to transmit data read from the prescription bag to the cash register 12.

Sniffer. The sniffer 14 is a conventional network monitoring tool for capturing data packets and decodes them using built-in knowledge of common protocols. The sniffer 14 is connected in series between the scanner 18 and the cash register 12 for filtering or intercepting prescription bar codes. Preferably, the sniffer 14 is constructed as a small-sized box attached on the length of a communications cable that connects the cash register 12 to the scanner 18. As bar codes are scanned by the scanner 18, the sniffer 14 filters the scanned data permitting only numbers relating to prescription medication to pass for being displayed by the monitor 20.

Credit Card Machine. The credit card machine 16 is a conventional card reader designed for obtaining numeric data, such as a magnetic strip reader, which reads account data directly from a credit card's magnetic strip. The credit card machine 16 is connected to the cash register 12 by conventional means for enabling account data encoded on a credit card to be transmitted to the cash register 12 to permit a credit card purchase of prescription medication. Such credit card machines are optional and not an essential part of the present invention.

Computer. The computer 22 can be a mainframe, a micro-computer, a personal computer or other computer connected to the sniffer 14 and the monitor 20. The computer 22 includes storage for a database containing a patient's confidential records, including records concerning each prescription medication ordered, and stores a patient's confidential form(s) as set forth below. The computer 22 may include a decoder or software for decoding and identifying bar code information. The computer 22 may be the same central computer which maintains inventory and price information, or may be a separate work station dedicated to maintaining the patient's confidential records. The information stored in the database may be downloaded daily to a floppy disk or compact disk for backup storage.

Monitor. The monitor 20 is connected to the computer 22 and directly or indirectly to the sniffer 14. The monitor 20 is preferably about four inches by eight inches in size, and has a screen for displaying a patient consultation form. When prescription medications are delivered, either directly to the patient or to an authorized person picking up medications for the patient, the prescription bag is scanned by the scanner 18. The prescription numbers and identification of the medication(s) are displayed in a patient consultation form on the monitor's screen, thereby enabling the patient or his agent to see all of the prescriptions being received. The patient consultation form also contains a space for the signature of the person accepting delivery of the prescription medication. The monitor 20 includes electronic circuitry for digitizing a signature traced on the monitor screen by a stylus or other device, and for sending an digitized image of the consultation form, including the signature, to the database on the computer 22 for storage.

If a question as to the delivery status of a prescription medication arises, information concerning the patient, including a list of all prescription numbers, the date and time delivered, and the person accepting delivery can be retrieved from the computer 22 database. In addition, an image of the patient consultation form for a particular prescription number, including the digitized signature, can be displayed on the monitor 20 screen.

The printer 24 is optional, and can be any conventional printer that is communicatively connected by common means to the computer 22 for enabling a list of prescription medications and associated prescription numbers, dates, times, and authorizing signatures to be printed.

Thus, an efficient and economical system has been disclosed for tracking patient confidentiality forms in a pharmacy.

It is to be understood that the present invention is not limited to the sole embodiment described above, but encompasses any and all embodiments within the scope of the following claims.

I claim:

1. A validating tracking system for tracking delivery of prescription medications from a pharmacy, the pharmacy having a computerized cash register and a scanner for scanning bar codes into the computerized cash register, the tracking system comprising:
   a) a sniffer connected to the scanner, the sniffer having means for filtering bar coded prescription numbers from data scanned by the scanner;
   b) a monitor having a screen for displaying the prescription numbers filtered by the sniffer, the monitor having electronic circuitry for digitizing a signature traced on the screen by a stylus; and
   c) a computer having a database for receiving, storing and retrieving prescription numbers from said sniffer, for entering, storing and retrieving information identifying prescription medications and patient information relating to the prescription numbers, for receiving, storing and retrieving digitized signatures traced on said monitor, and for storing, retrieving and displaying patient consultation forms on said monitor.

2. The validating tracking system according to claim 1, further comprising a printer connected to said computer for printing patient consultation forms.

3. The validating tracking system according to claim 1, wherein the computer further includes means for decoding and identifying bar coded prescription numbers.

4. The validating tracking system according to claim 1, wherein the monitor has a screen approximately 4 inches by 8 inches for displaying a patient consultation form.

5. A method of tracking the delivery of prescription medications to a patient by a pharmacy, comprising the steps of:
   a) associating at least one bar coded prescription number with a prescription order;
   b) for each said bar coded prescription number, entering information identifying a prescription medication and an associated patient into a database;
   c) when delivering the prescription medication, scanning said at least one bar coded prescription number;
   d) displaying a patient consultation form listing said at least one bar coded prescription number and information identifying the medication and patient;
   e) digitizing a signature traced on the patient consultation form by a person receiving delivery of the prescription medication; and
   f) storing said digitized signature in the database.

6. The method according to claim 5, further comprising the step of downloading records stored in the database to a backup storage disk daily.

7. The method according to claim 5, further comprising the step of printing the patient consultation form with the digitized signature of the recipient, a list of medications picked up, and the date and time of delivery.

8. The method according to claim 6, further comprising the step of displaying the patient consultation form on a monitor.

9. A tracking system for tracking delivery of prescription medications from a pharmacy, comprising:
   a) a bar code scanner for scanning bar coded prescription numbers;
   b) a sniffer connected to the scanner, the sniffer having means for filtering bar coded prescription numbers from data scanned by the scanner;
   c) a monitor having a screen for displaying the prescription numbers filtered by the sniffer, the monitor having electronic circuitry for digitizing a signature traced on the screen by a stylus; and
   d) a computer having a database means for receiving, storing and retrieving prescription numbers from said sniffer, for entering, storing and retrieving information identifying prescription medications and patient information relating to the prescription numbers, for receiving, storing and retrieving digitized signatures traced on said monitor, and for storing, retrieving and displaying patient consultation forms on said monitor.

10. The tracking system according to claim 9, further comprising an electronic cash register connected to said computer.

11. The tracking system according to claim 9, further comprising a credit card reader connected to said cash register.

12. The tracking system according to claim 9, further comprising a printer connected to said computer.

* * * * *